(12) United States Patent
Watanabe et al.

(10) Patent No.: US 6,349,229 B1
(45) Date of Patent: Feb. 19, 2002

(54) BODY FLUID TESTING DEVICE

(75) Inventors: Motokazu Watanabe; Shin Ikeda; Toshihiko Yoshioka, all of Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/445,557

(22) PCT Filed: Apr. 1, 1999

(86) PCT No.: PCT/JP98/01723
 § 371 Date: Mar. 7, 2000
 § 102(e) Date: Mar. 7, 2000

(87) PCT Pub. No.: WO99/52433
 PCT Pub. Date: Oct. 21, 1999

(30) Foreign Application Priority Data
 Apr. 9, 1998 (JP) .............................. 10-097563
 Jun. 11, 1998 (JP) .............................. 10-163263

(51) Int. Cl.[7] .............................. A61B 5/05; A61B 5/00
(52) U.S. Cl. .............................. 600/345; 600/309; 600/573; 600/576; 600/578; 600/579; 600/583
(58) Field of Search .............................. 600/345, 309, 600/346, 347, 348, 349, 352, 353, 354, 355, 356, 357, 359, 360, 361, 365, 573, 576, 578, 579, 583; 606/181–183

(56) References Cited

U.S. PATENT DOCUMENTS

| | | | | |
|---|---|---|---|---|
| 4,844,098 A | * | 7/1989 | Mitchen | 600/583 |
| 5,857,983 A | * | 1/1999 | Douglas et al. | 600/583 |
| 5,891,053 A | * | 4/1999 | Sesekura | 600/583 |
| 5,951,492 A | * | 9/1999 | Douglas et al. | 600/583 |
| 6,015,392 A | * | 1/2000 | Douglas et al. | 600/583 |
| 6,027,459 A | * | 2/2000 | Shain et al. | 600/573 |
| 6,045,541 A | * | 4/2000 | Matsumoto et al. | 604/313 |
| 6,048,352 A | * | 4/2000 | Douglas et al. | 606/181 |
| 6,144,869 A | * | 11/2000 | Berner et al. | 600/347 |
| 6,152,942 A | * | 11/2000 | Brenneman et al. | 606/181 |

FOREIGN PATENT DOCUMENTS

| | | |
|---|---|---|
| JP | 2-13549 | 1/1990 |
| JP | 2-95352 | 4/1990 |
| JP | 2-141414 | 11/1990 |
| JP | 9-285459 | 11/1997 |
| JP | 10-35508 | 2/1998 |

OTHER PUBLICATIONS

Japanese search report for PCT/JP99/01723 dated Jun. 15, 1999.
English translation of Form PCT/ISA/210.

* cited by examiner

*Primary Examiner*—Robert L. Nasser
*Assistant Examiner*—Navin Natnithithadha
(74) *Attorney, Agent, or Firm*—Ratner & Prestia, PC

(57) ABSTRACT

An examination system for bodily fluids includes a vessel-like examination unit having an opening, a sensor for examining the bodily fluids, and a bodily-fluids-oozing device. This system is further provided with a pump for decompressing the inside of the unit and an electromagnetic cross-valve for releasing the decompressed condition, or still further provided with humidifying means for supplying vapor inside the unit, in addition to the pump and the valve. As a result, the system produces a precise measurement with a little amount of bodily fluid.

11 Claims, 6 Drawing Sheets

BODY FLUID TESTING DEVICE

This application is a U.S. National Phase Application of PCT International Application PCT/JP98/01723.

TECHNICAL FIELD

The present invention relates to an examination system which oozes bodily fluids on skin surface and collects the oozed fluids, then examines the fluids with a sensor.

BACKGROUND ART

When blood sugar is examined in a conventional manner, an oozing device for bodily fluids such as a lancet is used for pricking skin in order to have the bodily fluids ooze there. Then an examination device for bodily fluids is applied there to collect specimen. This process requires numbers of operations before the examination is completed, and thus an automated examination system which sequentially carries out these operations is demanded.

One of the automated examination systems is disclosed in the Japanese Patent Application Non-examined Publication No. H10-33508. This system includes a tightening belt into which a finger is inserted, a needle for pricking the finger tip, and a sensor disposed nearby the needle. After being pricked with the needle, the finger is tightened with the belt so that bodily fluids ooze and contact with the sensor.

However, when the bodily fluids ooze over the skin surface, the fluids sometimes does not reach to the sensor, and this system thus cannot carry out the examination.

Further, because the bodily fluids are vaporized to a degree before they reach to the sensor, a precise examination is not expected particularly when the bodily fluids oozed are in a little quantity.

The present invention addresses the problems discussed above, and aims to provide an examination system for bodily fluids. This system of the present invention can supply the bodily fluids free from errors to a specimen collector of a sensor, even when the bodily fluids oozed by the examination system are in a little quantity.

Another object of the present invention is to provide an examination system for bodily fluids, and which suppresses evaporation from the bodily fluids oozed so that the examination can produce a precise result.

SUMMARY OF THE INVENTION

An examination system of the present invention aims to solve the problems discussed above and comprises the following elements:

a vessel-like examination unit having an opening in front;
  decompressing means for decompressing the inside of the unit; and
  a specimen collector provided in the unit and facing the opening.

The present invention also provides an examination system which includes a bodily-fluids-oozing-device in the unit discussed above.

The present invention provides another examination system which comprises the following elements:

a vessel-like examination unit having an opening in front;
  humidifying means for humidifying the inside of the unit;
  a bodily-fluids-oozing-device; and
  a specimen collector provided in the unit and facing the opening.

The present invention further provides an examination system which includes decompressing means facing the opening in the examination unit.

The specimen collector preferably incorporates with a sensor, and a specimen-supplying-outlet of the device in the unit preferably faces the opening.

The present invention still further provides an examination system which comprises the following elements:

a vessel-like examination unit having an opening in front;
  decompressing means for decompresses the unit;
  decompress releasing means for restoring a decompressed unit to atmospheric pressure;
  a bodily-fluids-oozing-device;
  a specimen collector provided in the unit and facing the opening;
  a sensor having an electrode system for contacting with the specimen supplied from the specimen collector and outputting information about the specimen as an electric signal from the electrode system;
  determining means for determining a measured value with the electric signal; and
  a controller for controlling the decompressing means, decompress-releasing-means and sensor.

This examination system allows the decompress-releasing-means to function after the sensor outputs an electric signal. It is preferable for this system that the decompressing means functions after the bodily-fluids-oozing-device functions as well as the decompress-releasing-means functions after the sensor outputs an electric signal.

The present invention yet provides another examination system which comprises the following elements:

a vessel-like unit having an opening in front;
  humidifying means for humidifying the inside of the unit;
  decompressing means for decompressing the inside of the unit;
  decompress releasing means for restoring a decompressed condition to atmospheric pressure;
  a bodily-fluids-oozing-device;
  a specimen collector provided in the unit and facing the opening;
  a sensor having an electrode system for contacting with the specimen supplied from the specimen collector and outputting information about the specimen as an electric signal from the electrode system;
  determining means for determining a measured value with the electric signal; and
  a controller for controlling the humidifying means, decompressing means, decompress-releasing-means and sensor.

This examination system allows the bodily-fluids-oozing-device to function after the humidifying means functions as well as the decompress-releasing-means to function after the oozing device functions, and the decompress-releasing-means to function after the sensor outputs an electric signal.

The examination systems discussed above produce the following advantages:

In one of the embodiments of the systems, urge the opening of unit against skin—from which bodily fluids are to be sucked—thereby blocking up the opening, then have the decompressing means decompress the inside of the unit for rising the skin within the opening so that the bodily fluids can be supplied to the specimen collector with ease.

The bodily-fluids-oozing-device, which oozes bodily fluids from the skin, can be arranged in the examination unit so that the opening of the unit faces the oozing device, whereby a series of operations such as oozing and sucking bodily fluids can be sequentially carried out.

In another embodiment of the systems, urge the opening of unit against skin—from which bodily fluids are to be sucked—thereby blocking up the opening, then have the humidifying means humidify the inside of the unit. This prevents the bodily fluids oozed by the bodily-fluids-oozing-device from being vaporized. The oozing device is disposed in the unit so that the evaporation can be effectively suppressed.

When the inside of the unit is decompressed, the bodily fluids are subject to evaporation, this system thus allows the humidifying means to work before the decompressing means starts to work in order to humidify the inside of the unit in advance.

As the humidifying means, e.g. a water bowl—having a heater or an ultrasonic-wave-generator on the bottom—can be used. The upper section of the bowl communicates with the examination unit so that vapor produced from the water in the bowl flows into the unit, in particular, into the openingside.

A fan disposed at the communicating section between the unit and the bowl can efficiently run the vapor produced in the bowl into the unit.

When a humidity inside the unit rises so high, the inner wall of the unit and a surface of the sensor holder are sometimes dewed. If the dews drop onto the skin surface, the bodily fluids are thinned. This adversely affects the examination result. It is therefore preferable to dispose a humidity-sensor-probe in the unit for monitoring the humidity therein when bodily, fluids are examined. Considering an effective prevention against the evaporation, the humidity in the unit preferably ranges from 60 to 70%.

When a decompressing pump is used as the decompressing means, the inside of the unit is quickly decompressed so that the bodily fluids can be quickly supplied to the specimen collector.

Further, when decompress-releasing-means is disposed in the unit for restoring the decompressed condition inside the unit to atmospheric pressure, it prevents air from flowing rapidly into the unit at removing the unit from the skin after the examination. As a result, the bodily fluids are not scattered.

An operation program of the examination system can be set so that the decompress-releasing-means works at the same time on or with some delay of completing the examination. This can notify a user of weak eyes with a feeling of skin stretch that the user is still under the examination.

DESCRIPTION OF THE PREFERRED EMBODIMENTS

Exemplary embodiments of the present invention are demonstrated hereinafter with reference to the accompanying drawings.

(Exemplary Embodiment 1)

Figure 1:
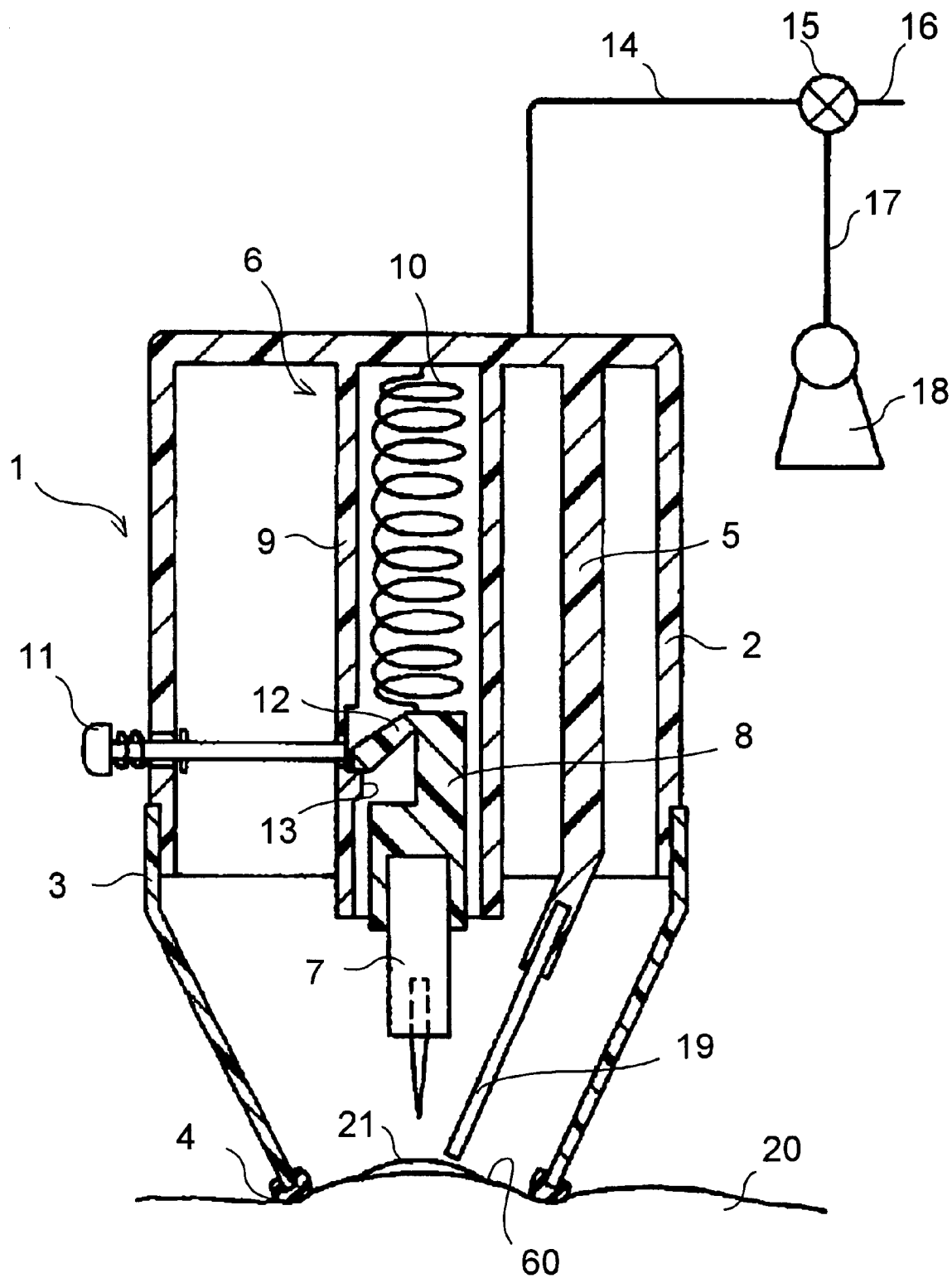
FIG. 1 is a cross section illustrating a schematic construction of an examination system for bodily fluids in accordance with a first exemplary embodiment of the present invention.

FIG. 1 shows a construction of an examination system for bodily fluids in accordance with the first exemplary embodiment of the present invention.

Examination unit 1 comprises cylinder 2 having a bottom plate and cap 3 screwed detachably on the opening of cylinder 2. An opening of the unit, formed at the tip of cap 3, is e.g. an oval having 15 mm longer diameter and 10 mm shorter diameter. This opening is equipped with adapter 4 made of rubber to protect skin and achieve tighter adherence to the skin.

Sensor holder 5 and bodily-fluids-oozing-device 6 are disposed inside of the unit 1. Sensor holder 5 is mounted with sensor 19 at its tip, and includes a terminal contacting with an electrode terminal of the sensor and a lead-wire coupling this terminal to an examining section (not shown). Oozing device 6 comprises needle holder 8 to which needle supporter 7 is mounted, while a needle is fixed to the tip of needle supporter 7, tube 9 guiding needle holder 8, spring 10 protruding needle holder 8, and switch 11.

Needle holder 8 is unitarily formed with stopper 12 which is urged toward left in the drawing by stopper's own elasticity. This stopper 12 engages with step 13 provided in tube 9 so that needle holder 8 remains within tube 9. When switch 11 presses stopper 12 rightward and releases the engagement with step 13, needle holder 8 protrudes to the opening of the unit by the elasticity of spring 10.

A closed top section of unit 1 is coupled to electromagnetic cross-valve 15 by pipe 14. Electromagnetic valve 15 is coupled to decompressing pump 18 via pipe 17 and to releasing pipe 16. In this embodiment, sensor holder 5 is equipped with sensor 19 for measuring blood sugar. A specimen-supplying-outlet at the tip of sensor 19 works as a specimen collector. The specimen supplying outlet sucks blood by capillarity.

A tip of oozing device 6 is away from skin 20 comparing with the specimen collector of sensor 19. The bodily fluids oozed have thus no chance to contact with the tip of device 6 when the inside of unit 1 is decompressed. As shown in FIG. 1, it is preferable to set a place—to be pricked by the needle of oozing device 6—at or near the center of the opening of the unit because bodily fluids 21 are accumulated in a top of skin swelling up as marked with 60. It is also preferable to arrange the specimen collector of the sensor near to the center of the unit's opening because a space between the collector and the skin becomes shorter.

The opening of the unit is preferably shaped like a round or an oval rather than a square in order to block up the opening with the skin airtightly. The unit per se is preferably made of transparent material such as glass or plastic, and plastic is more preferable from the standpoint of light weight and safety. As the decompressing means, an electric-driven decompressing pump is preferable because of its strong decompressing power. A vacuum pump is more preferable among others because of its smaller size.

An operation and an effect of this examination system are demonstrated hereinafter.

First, press the opening of unit 1 against skin 20 such as a finger thereby blocking up the opening. Next, prick the skin with oozing device 6 so that bodily fluids are oozed and sucked. In this embodiment, blood is taken as an example and is sucked. The needle supported by needle supporter 7 is biased by spring 10 and reaches to the skin, then pricks slightly the skin surface. Blood thus oozes from the skin surface. At this moment, decompressing pump 18 coupled to the unit lowers the inside pressure of the unit from atmospheric pressure. The skin swells up toward the inside of the unit due to this decompress, and the blood on the skin surface contacts with the specimen collector of the sensor, then the blood is supplied to the sensor. The finger tip swells to a degree; however, the decompressing means raises the skin so that the blood can contact with the specimen collector of the sensor, thus individual differences in height of the skin raised does not affect the specimen collection. Further, when a user of diabetes, e.g. and being suffered from the weak eye due to the complications, uses this examination system, the bodily fluids are supplied to the sensor free from failures. Because examination unit 1 can be moved arbitrarily, the user can prick any spot of the body such as finger, palm, back of the hand, arm, belly, earlobe and the like.

In the first exemplary embodiment, bodily-fluids-oozing-device 6 uses the needle biased by spring 10; however, laser beam and the like, which prick slightly the skin surface, can be used with the same effect.

The sensor is disposed within the unit; however, as far as the specimen collector is disposed within the unit, the sensor per se can be disposed outside of the unit.

The bodily-fluids-oozing-device is not always equipped to unit 1. When the device is not equipped to the unit, an oozing device available on the market, e.g. a lancet, is used to ooze the bodily fluids. Then the unit is applied to the spot where the bodily fluids ooze, and the decompressing means decompresses the inside of the unit thereby raising the skin for supplying the bodily fluids to the sensor.

Figure 2:
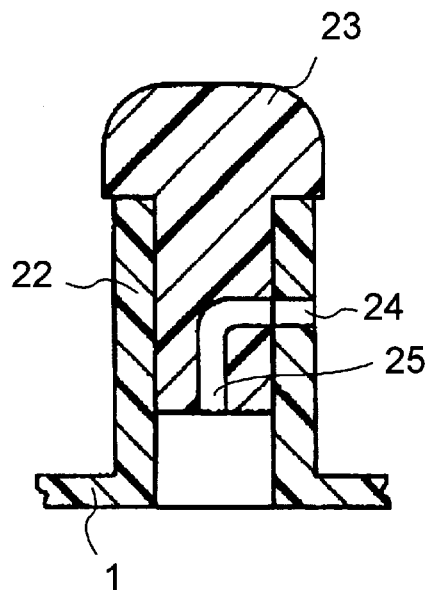
FIG. 2 is a cross section of an essential part of a decompress-releasing device of the examination system shown in FIG. 1.

Electromagnetic cross-valve is used as the decompress-releasing-means in this first embodiment; however, the decompress-releasing-means separated from the cross valve can be provided to the unit. As shown in FIG. 2, for instance, pipe 22 communicating with the inside of the unit is provided to a top section of unit 1, and rotary valve 23 is mounted to this pipe. Rotary valve 23 is rotated manually to have air-hole 25 communicate with air-permeable-hole 24 punched on pipe 22 so that the decompressed status in examination unit 1 can be released.

If unit 1 is removed from the skin being kept the decompressed status, the air flows into unit 1 abruptly thereby scattering the bodily fluids oozed. This may dirty the circumference. The decompress-releasing-means thus releases the decompressed condition so that the pressure inside the unit is restored to atmospheric pressure, and the bodily fluids have no chance to scatter. Further, this arrangement allows a user to remove the unit from the skin with ease free from a forcible manner. When the skin is stretched as strong as a user feels a pain due to decompressing, the rotary valve is rotated thereby releasing quickly the decompressed condition to remove the unit from the skin with ease.

The bodily fluids—which this examination system examines—include blood, lymphatic fluid, intercellular fluid and perspiration, which can be collected from skin surface.
(Exemplary Embodiment 2)

Figure 3:
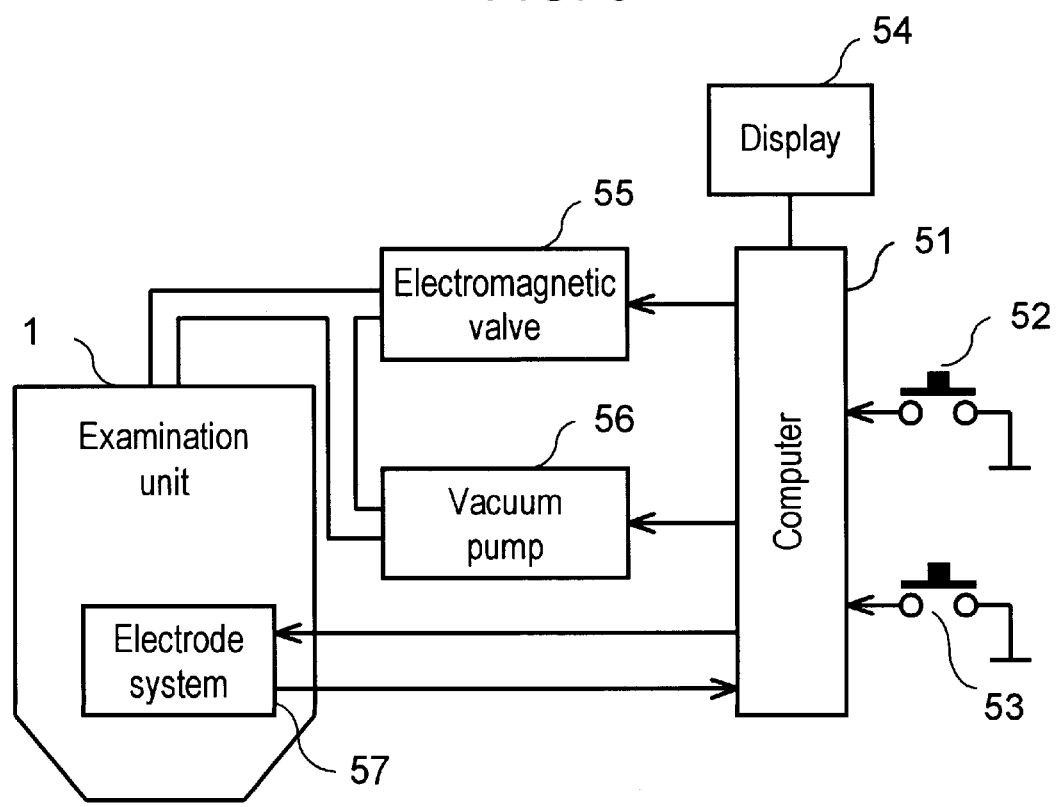
FIG. 3 is a block diagram illustrating a circuit of the examination system in accordance with a second exemplary embodiment of the present invention.

FIG. 3 is a block diagram illustrating a circuit of an examination system in accordance with the second exemplary embodiment.

A diabetic patient measures his own blood sugar by himself as a routine work. The patient is sometimes suffered from detachment of retina, one of complications of diabetes, and in the worst case the patient loses his eyesight. Even if the patient eventually has weak eyes, he must measure the blood sugar routinely. When a patient of weak eyes examines his own blood, it is not easy for the patient to determine whether the blood oozes on the skin or not.

According to the second embodiment, a patient of weak eyes can examine his own blood free from failures using a sensor with an auto-start function and decompressing means for decompressing the inside of the unit. In this second embodiment, a needle is used as bodily-fluids-oozing-device same as the first embodiment and a vacuum pump is used as the decompressing means. Blood is taken as an example of bodily fluids to be examined. The vacuum pump is coupled to the unit as shown in FIG. 1 and can decompress the inside of the unit.

In FIG. 3, examination unit 1, to which a sensor is mounted for collecting and examining the bodily fluids, communicates with electromagnetic valve 55 and vacuum pump 56 via pipes. Computer 51 controls electromagnetic valve 55 and vacuum pump 56 thereby decompressing the inside of the unit or releasing the decompressed condition. Computer 51 further applies a voltage to electrode system 57 provided to the sensor and receives an electric signal from electrode system 57. It also issues a next instruction based on the electric signal, determines a measured value by calculating the electric signals, and outputs the instruction as well as the measured value on display 54.

Computer 51 is initialized by turning main-switch 52 on and is loaded with a program which drives vacuum pump 56 by activating the bodily-fluids-oozing-device.

Figure 4:
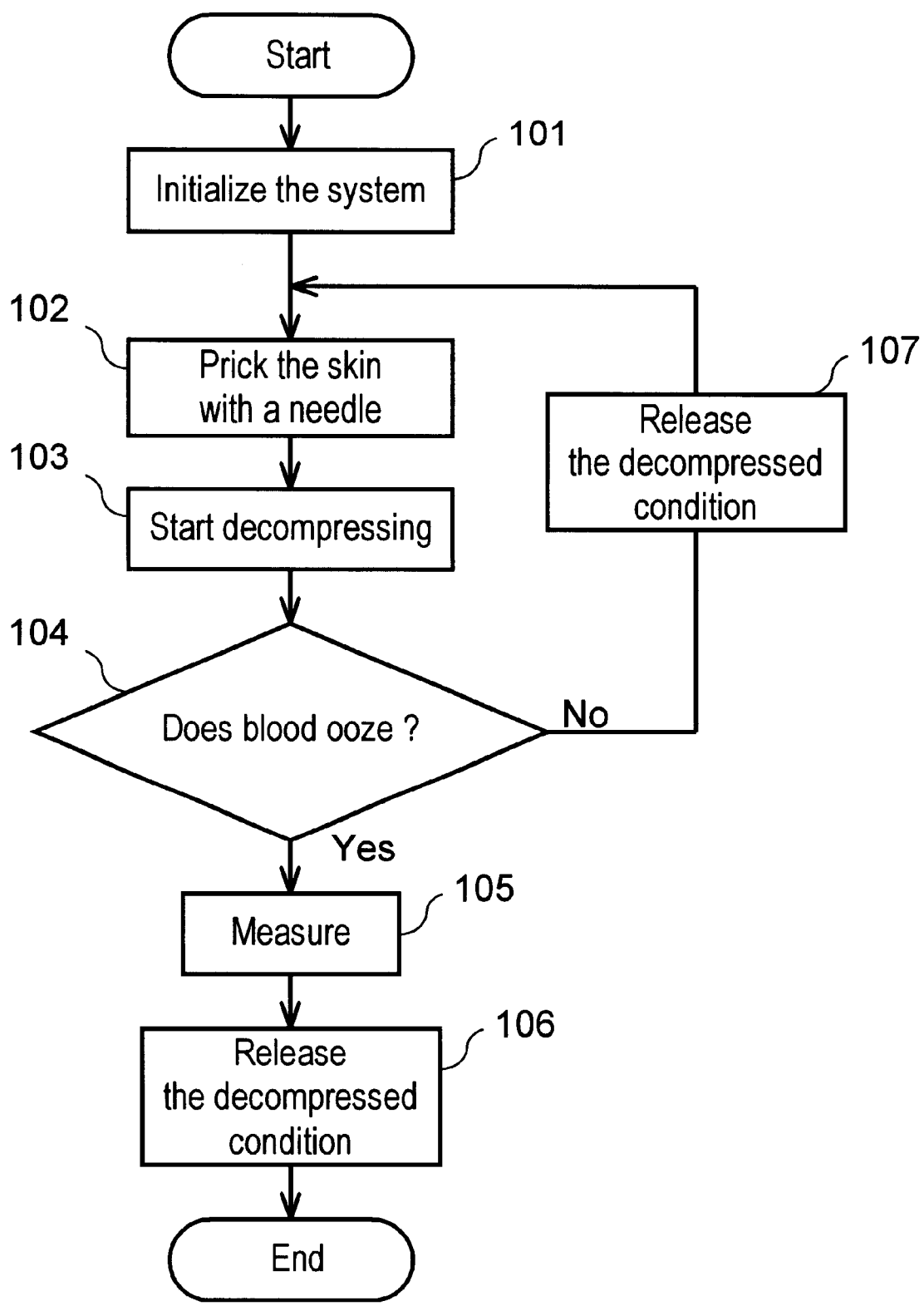
FIG. 4 is a flowchart illustrating an operation of the examination system.

An operation of this system is demonstrated with reference to the flowchart shown in FIG. 4.

First, apply the opening of unit 1 to the skin, and turn on main switch 52 of computer 51 to initialize the system, such as clearing the memories (Step 101). Then turn on switch 53 of the bodily-fluids-oozing-device to prick the skin with the needle (Step 102). At this moment, if the needle substantially reaches to the skin, blood oozes.

After a while of switch 53 being turned on, vacuum pump 56 discharges the air from unit 1, i.e. decompress-operation starts (Step 103).

In step with the progress of decompressing operation inside of the unit, the skin urged tightly to unit 1 is sucked and swells up inside unit 1 and eventually contacts with the specimen collector of the sensor. At this moment, if the blood has oozed, the blood is supplied to the specimen collector. A voltage has been applied between at least two electrodes of the sensor, and computer 51 detects the availability of specimen through fluid communication between the electrodes when the blood is supplied to the sensor (Step 104), and starts measuring (Step 105). After the measurement, decompress-releasing-means releases the decompressed condition in unit 1 (Step 106). After the condition inside the unit is restored to atmospheric pressure, examination unit 1 is removed from the skin, and the examination is completed.

In Step 104, when computer 51 does not detect fluid communication between the electrodes and then determines that no blood oozes on the skin surface after a given period e.g. 15 seconds of starting the decompression, the decompressed condition in unit 1 is released (Step 107). Further, this is displayed on display 54, or alarm sound is produced so that an examiner can notice that the blood is not collected. Because the needle insufficiently pricks the finger, the system cannot collect the blood. Therefore, urge the finger against unit 1, for instance, to shorten the distance between the skin and the needle, and repeat Step 102 and onward.

When another sensor—which measures a specific component in the bodily fluids with the amount of current running between the electrodes of the electrode system—is used, an intense shock to the sensor would run noise current, which adversely affects the examination. Since a user of weak eyes, in particular, cannot monitor the progress of examination by his eyes, this adverse-influence sometimes prevents the examination from being carried out in a normal way.

In this second embodiment, the inside of unit 1 is thus decompressed before the sensor starts to measure, and the decompressed condition is released after the measurement is completed. In other words, the examination system is programmed so that the decompress-releasing-means works at the same time or after some delay when the examination is completed. This arrangement allows a user to feel that he is still under the examination although he cannot monitor whether the needle pricks his skin or not in Step 102. Because the inside of unit 1 is decompressed before the sensor starts to measure, the user can feel that he is under the examination in Step 103, where the decompress operation starts, through Step 106, where the decompressed condition is released.

As a result, a user of weak eyes can avoid applying shocks to the examination system during the examination and prevent the adverse influence to the bodily-fluids examination.

When decompressing and releasing thereof are repeated often, a motor-driven pump is preferably used for the decompressing means because it starts decompressing promptly after power-on.

(Exemplary Embodiment 3)

Figure 5:
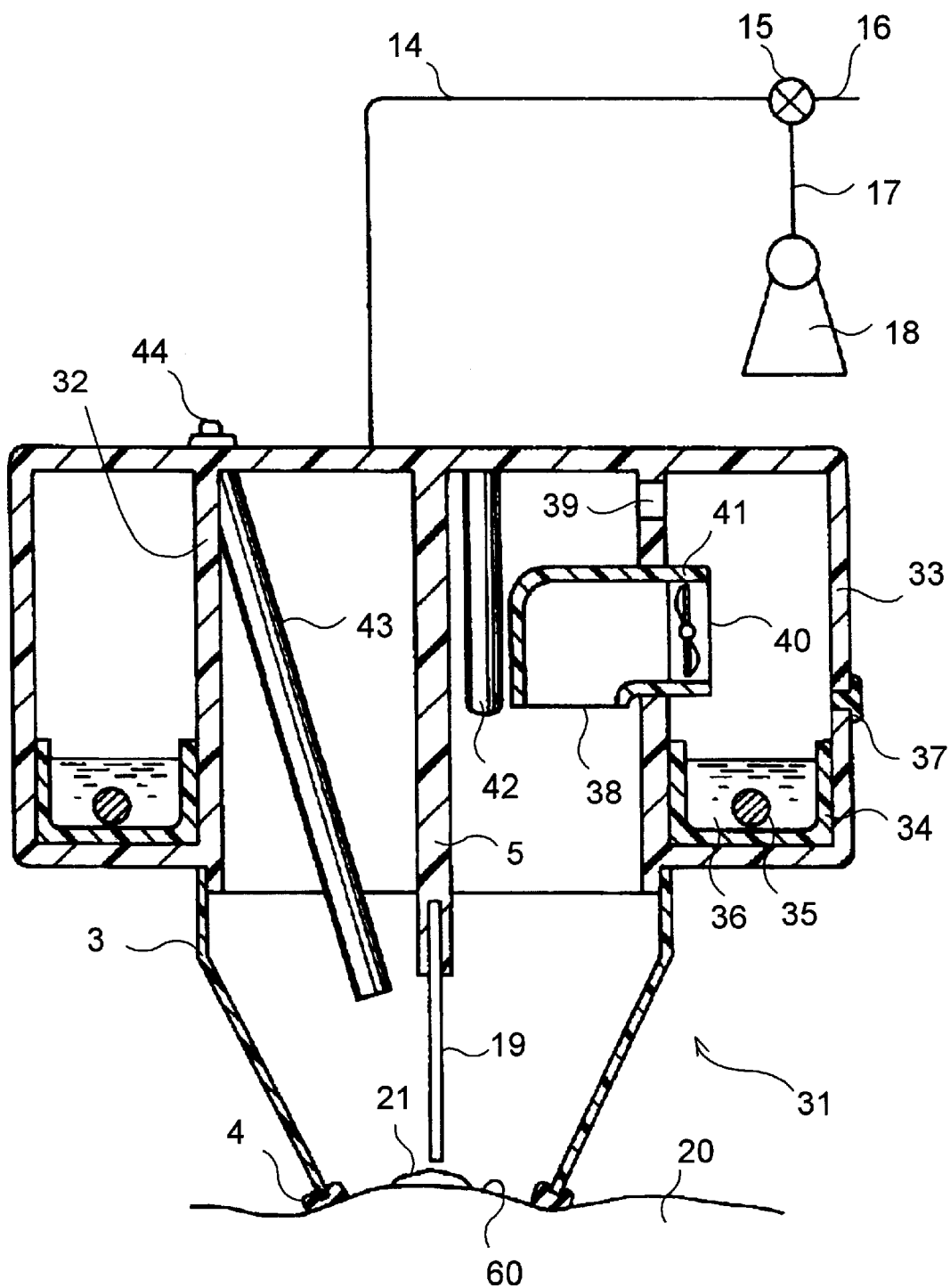
FIG. 5 is a cross section illustrating part of schematic construction of an examination system in accordance with a third exemplary embodiment of the present invention.

FIG. 5 illustrates a structure of an examination system for bodily-fluids in accordance with the third exemplary embodiment.

Examination unit 31 comprises double-cylinder with a bottom plate, and cap 3 detachably screwed on an opening of inner cylinder 32. Outer cylinder 33 blocks up its lower end by itself. An opening of unit 31 is formed at tip of cap 3 and is equipped with adapter 4 made of rubber.

Outer cylinder 33 communicates with inner cylinder 32 via blower 38 and air hole 39. Blower 38 comprises pipe 41 and fan 40 disposed in pipe 41.

A humidifier comprises blower 38, outer cylinder 33, water bowl 34 disposed within cylinder 33, and heater 35 disposed within the bowl. Water bowl 34 is filled up with water 36. On the outer wall of cylinder 33, water-supply-outlet is provided for supplying water 36 into bowl 34. When the water is supplied, cap 37 is removed from the outlet.

Sensor holder 5, bodily-fluids-oozing device 43, and humidity-sensor probe 42 are disposed inside of cylinder 32.

Humidity-sensor probe 42 has a lead-wire coupling the probe to a controller (not shown). Sensor holder 5 is equipped with sensor 19 at its tip, and has a terminal contacting with an electrode terminal of the sensor as well as a lead-wire coupling the terminal to an examining section (not shown).

Bodily-fluids-oozing device 43 comprises a laser beam radiator which irradiates laser beam by depressing switch 44, and has a lead wire coupling the device 43 to a power supply (not shown).

Laser beam radiator 43 is placed so that laser beam hits the center or around the center of the opening of unit 31. Sensor 19 is arranged to face the opening center so that a specimen supplier of the sensor is located near the opening-center of unit 31.

An operation and an effect of this examination system is demonstrated hereinafter.

First, warm up water 36 in bowl 34 by heater 35 to raise the humidity in the humidifier. Then blow the air of the humidifier into cylinder 32 by fan 40 to humidify the inside of cylinder 32. In this condition, urge the opening of unit 31 against skin 20, e.g. a finger, to block up the opening. Then control the humidity inside cylinder 32 at ca. 65% with humidity-sensor probe 42.

Next, depress switch 44 to irradiate laser beam, which pricks the skin surface and results in oozing bodily fluid 21. Then decompress the inside of cylinder 32 with decompressing pump 18 coupled to cylinder 32. The skin swells up toward the inside of the unit and the bodily fluid contacts with the specimen supplier. Finally the bodily fluid is supplied to the sensor.

(Exemplary Embodiment 4)

Figure 6:
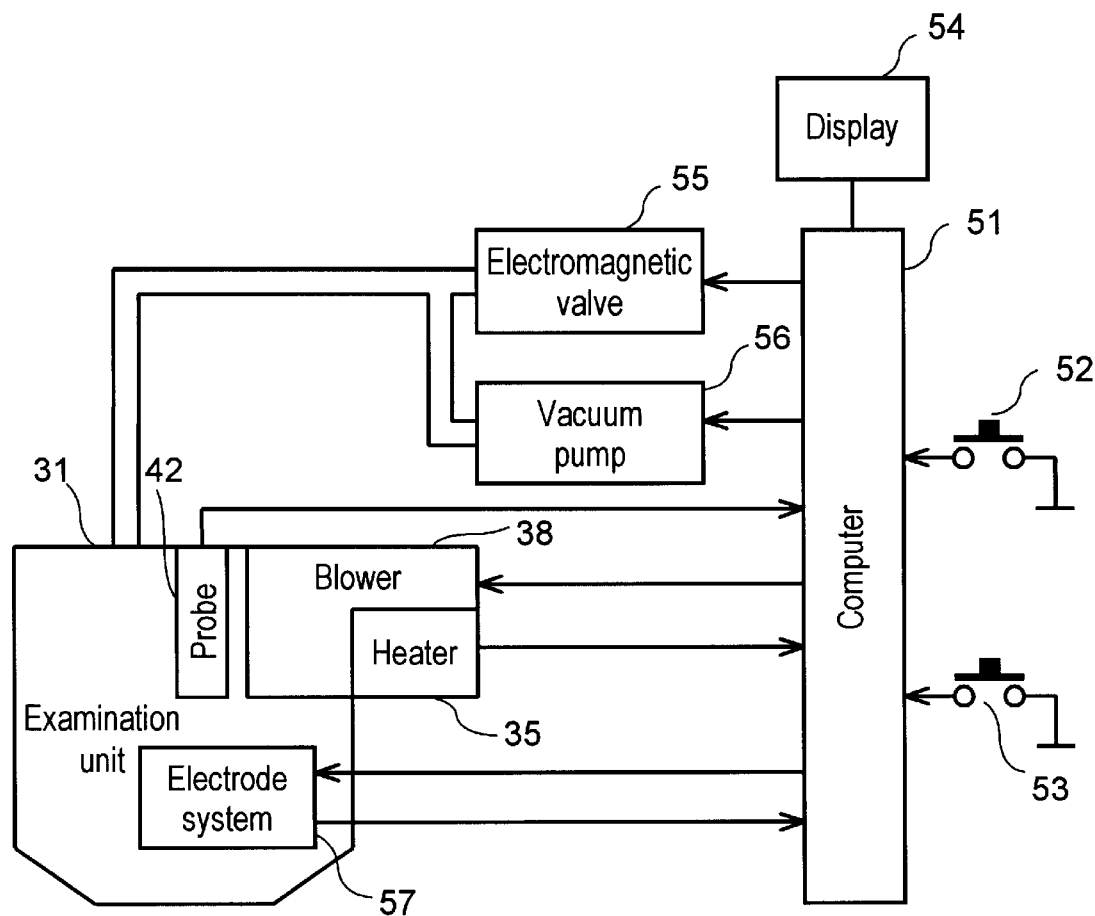
FIG. 6 is a block diagram illustrating a circuit of an examination system in accordance with a fourth exemplary embodiment of the present invention.

FIG. 6 is a block diagram illustrating a circuit of an examination system for bodily fluids in accordance with the fourth exemplary embodiment.

In FIG. 6, a sensor for collecting and examining the bodily fluids is mounted to examination unit 31, which communicates with electromagnetic valve 55 as well as vacuum pump 56 via pipes. Computer 51 controls valve 55 and pump 56 to decompress the inside of unit 31 or release the decompressed condition.

Computer 51 applies a voltage to electrode system 57 provided to the sensor and receives an electric signal from electrode system 57. It also issues a next instruction based on the electric signal, calculates the electric signals and then determines a measured value, and outputs the instruction as well as the measured value on display 54.

Computer 51 also receives the electric signal regarding the humidity from humidity-sensor probe 42, and based on the humidity information it controls on-off operation of the fan of blower 38 as well as on-off operation of heater 35.

Computer 51 is initialized when main-switch 52 is turned on, and then allows heater 35 and blower 38 to humidify the inside of unit 31. When the computer determines that the humidity is not less than 50% based on the humidity information from sensor probe 42, the computer is programmed to firstly activate the laser beam radiator and then drive vacuum pump 56.

For instance, when humidity-sensor probe 42 detects a humidity as high as 80%, computer 51 is programmed to turn off the fan of blower 38 and heater 35.

Figure 7:
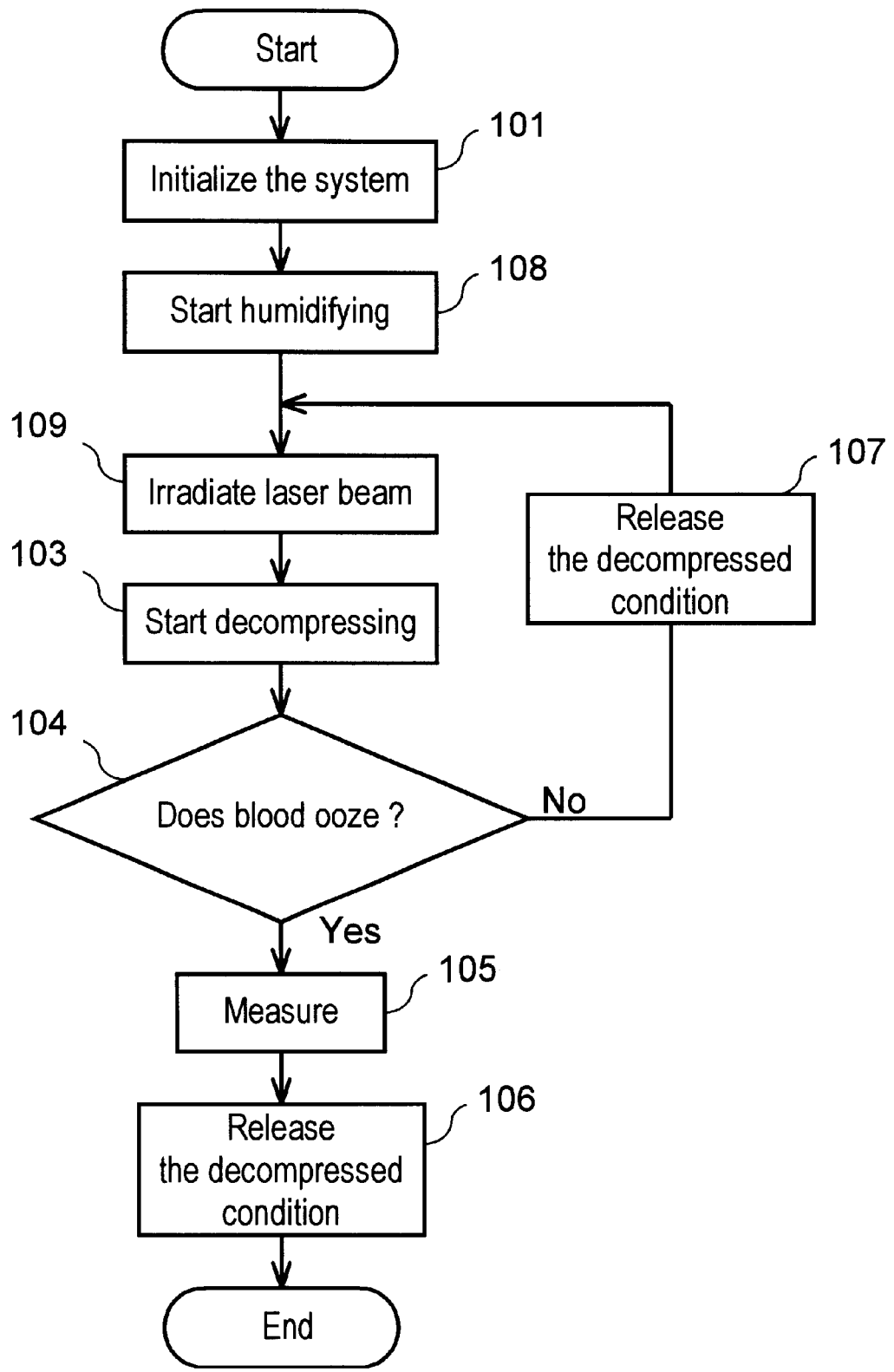
FIG. 7 is a flowchart illustrating an operation of the examination system.

An operation of this system is demonstrated with reference to the flowchart shown in FIG. 7.

First, turn on main-switch 52 of computer 51 to initialize the system, which includes clearing the memories (Step 101).

Second, power on heater 35 to warm up water in the bowl, then activate blower 38 to humidify the inside of unit 31 (Step 108). This humidifying is preferably started immediately after the system is initialized because the inside of unit 31 has been desirably humidified at the laser beam radiation in order to avoid vaporizing the bodily fluids.

Third, apply the opening of unit 31 to the skin, and turn on switch 44 of the laser-beam-radiator to ooze bodily fluids from the skin (Step 109). After a while of turning on switch 44, pump 56 starts decompressing (Step 103). Then repeat the same processes as described in the second embodiment which is illustrated in FIG. 4.

According to the examination system for bodily fluids discussed above, the decompressing means decompresses the inside of the unit to swell the skin up toward the specimen collector, and even the bodily fluids oozed are in a little amount, the fluids can be supplied to the sensor free from failures.

Since the humidifying means humidifies the inside of the unit, a little amount of bodily fluid oozed out is prevented from being vaporized so that the density change of the respective fluid components can be minimized. As a result, a precise examination is expected.

Further, a user of weak eyes can feel that his skin is stretched during the measurement, and thus the system can carry out the examination free from any shocks and the like which adversely affect the sensor.

INDUSTRIAL APPLICABILITY

The present invention provides an examination system for bodily fluids. The system comprises a vessel-like examination unit having an opening, a sensor for examining the bodily fluids, and a bodily-fluids-oozing device. The present invention also provides this system with a pump for decompressing the inside of the unit and an electromagnetic cross-valve for releasing the decompressed condition, or further provides this system with humidifying means for supplying vapor inside the unit, in addition to the pump and the valve. As a result, the system produces a precise measurement with a little amount of bodily fluid.

What is claimed is:

1. A bodily-fluids-examination-system comprising:
   a vessel-like examination unit having an opening in front;
   decompressing means for decompressing an inside of said unit;
   a sensor holder in said unit;
   a specimen collector disposed in said unit and facing the opening; and
   a bodily-fluids-oozing-device.

2. The bodily-fluids-examination-system as defined in claim 1, wherein said bodily-fluids-oozing-device includes one of a needle and a laser beam radiator.

3. The bodily-fluids-examination-system as defined claim 1, further comprising decompress-releasing-means for restoring a decompressed condition in said unit to atmospheric pressure.

4. A bodily-fluids-examination-system comprising:
   a vessel-like examination unit having an opening in front;
   humidifying means for humidifying an inside of said unit;
   a bodily-fluids-oozing-device; and
   a specimen collector disposed in said unit and facing the opening.

5. The bodily-fluids-examination-system as defined in claim 4 further comprising decompressing means for decompressing the inside of said unit.

6. The bodily-fluids-examination-system as defined claim 5, further comprising decompress-releasing-means for restoring a decompressed condition in said unit to atmospheric pressure.

7. The bodily-fluids-examination-system as defined in claim 5, wherein said bodily-fluids-oozing-device includes one of a needle and a laser beam radiator.

8. The bodily-fluids-examination-system as defined in claim 4, wherein said bodily-fluids-oozing-device includes one of a needle and a laser beam radiator.

9. A bodily-fluids-examination-system comprising:
   a vessel-like examination unit having an opening in front;
   decompressing means for decompressing an inside of said unit;
   decompress-releasing-means for restoring a decompressed condition in said unit to atmospheric pressure;
   a bodily-fluids-oozing-device;
   a specimen collector disposed in said unit and facing the opening;
   a sensor, having an electrode system for contacting with a specimen supplied from said specimen collector, for outputting information regarding the specimen as an electric signal from the electrode system;
   determining means for determining a measured value of the specimen based on the electric signal;
   a controller for controlling said decompressing means, said decompress-releasing-means and said sensor,
   wherein said system allows said decompress-releasing-means to function after said sensor outputs the electric signal.

10. A bodily-fluids-examination-system comprising:
    a vessel-like examination unit having an opening in front;
    decompressing means for decompressing an inside of said unit;
    decompress-releasing-means for restoring a decompressed condition in said unit to atmospheric pressure;
    a bodily-fluids-oozing-device;
    a specimen collector disposed in said unit and facing the opening;
    a sensor, having an electrode system for contacting with a specimen supplied from said specimen collector, for outputting information regarding the specimen as an electric signal from the electrode system;
    determining means for determining a measured value of the specimen based on the electric signal;
    a controller for controlling said decompressing means, said decompress-releasing-means and said sensor,
    wherein said system allows said decompressing means to function after said bodily-fluids-oozing-device operates as well as said decompress-releasing-means to function after said sensor outputs the electric signal.

11. A bodily-fluids-examination-system comprising:
    a vessel-like examination unit having an opening in front;
    humidifying means for humidifying an inside of said unit;
    decompressing means for decompressing the inside of said unit;
    decompress-releasing-means for restoring a decompressed condition in said unit to atmospheric pressure;
    a bodily-fluids-oozing-device;
    a specimen collector disposed in said unit and facing the opening;
    a sensor, having an electrode system for contacting with a specimen supplied from said specimen collector, for outputting information regarding the specimen as an electric signal from the electrode system;
    determining means for determining a measuring value of the specimen based on the electric signal;
    a controller for controlling said humidifying means, said decompressing means, said decompress-releasing-means and said sensor,
    wherein said system allows said bodily-fluids-oozing-device to function after said humidifying means operates, and also allows said decompressing means to function after said bodily-fluids-oozing-device operates as well as said decompress-releasing-means to function after said sensor outputs the electric signal.

* * * * *

UNITED STATES PATENT AND TRADEMARK OFFICE
CERTIFICATE OF CORRECTION

PATENT NO.    : 6,349,229 B1
DATED         : February 19, 2002
INVENTOR(S)   : Watanabe et al.

It is certified that error appears in the above-identified patent and that said Letters Patent is hereby corrected as shown below:

<u>Title page,</u>
Item [86], "PCT/JP98/01723" should read -- PCT/JP99/01723 --.

Signed and Sealed this

Fourteenth Day of January, 2003

JAMES E. ROGAN
*Director of the United States Patent and Trademark Office*